United States Patent [19]

Hochberg

[11] Patent Number: 4,989,615

[45] Date of Patent: Feb. 5, 1991

[54] APPARATUS FOR NON-INVASIVE MONITORING OF UTERINE CONTRACTIONS

[75] Inventor: Howard M. Hochberg, Woodinville, Wash.

[73] Assignee: International Biomedics, Inc., Bothell, Wash.

[21] Appl. No.: 363,322

[22] Filed: Jun. 6, 1989

Related U.S. Application Data

[63] Continuation-in-part of Ser. No. 142,943, Jan. 12, 1988, abandoned, which is a continuation-in-part of Ser. No. 857,021, Apr. 29, 1986, abandoned.

[51] Int. Cl.$^5$ .............................................. A61B 5/103
[52] U.S. Cl. ..................................... 128/774; 128/775; 128/778
[58] Field of Search ............................... 128/774–775, 128/778, 780, 782, 748, 686, 327, 721

[56] References Cited

U.S. PATENT DOCUMENTS

| 1,637,829 | 8/1927 | Lurie | 128/802 |
| 3,520,294 | 7/1970 | Fuzzell et al. | 128/775 |
| 3,726,273 | 4/1973 | Cole | 128/778 |
| 3,752,148 | 8/1973 | Schmalzbach | 128/686 |
| 3,913,563 | 10/1975 | Ball | 128/775 |
| 3,945,373 | 3/1976 | Tweed et al. | 128/778 X |
| 4,114,188 | 9/1978 | Carter et al. | 128/778 X |
| 4,122,837 | 10/1978 | Leonard | 128/774 |
| 4,399,809 | 8/1983 | Baro et al. | 128/327 X |
| 4,592,342 | 1/1986 | Salmasian | 128/118.1 X |
| 4,622,957 | 11/1986 | Curlee | 128/118.1 X |
| 4,640,295 | 2/1987 | Isaacson | 128/775 X |
| 4,747,415 | 5/1988 | Lavoisier | 128/774 |

FOREIGN PATENT DOCUMENTS 0230768 12/1985 Fed. Rep. of Germany ...... 128/775

OTHER PUBLICATIONS

LaCroix, G. E.; Monitoring Labor by an External Tokodynamometer; American Journal of Obstetrics and Gynecology; 1968; vol. 101, p. 111.

Smyth, C. N., The Guard-Ring Tocodynamometer; Journal of Obstetrics and Gynecology of the British Empire; 1957; vol. 64, p. 59 (referencing the above patent document).

Primary Examiner—Max Hindenburg
Assistant Examiner—J. P. Lacyk
Attorney, Agent, or Firm—Graybeal, Jensen & puntigam

[57] ABSTRACT

An apparatus which includes a bladder element (10) which is at least partially filled with fluid, a belt-like element (12) which holds the bladder against the patient's abdomen with some pressure, and a pressure monitoring device (18) which is connected to the bladder (10) to detect changes in the pressure of the fluid in the bladder (10) as the abdomen hardens due to uterine contractions.

5 Claims, 4 Drawing Sheets

FIG.8
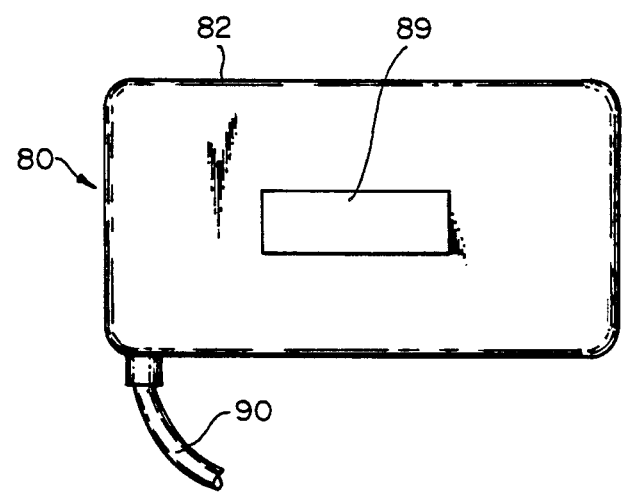
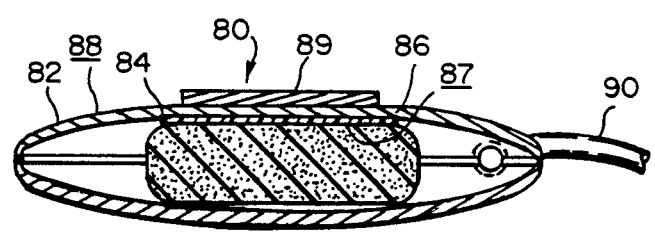
FIG.9
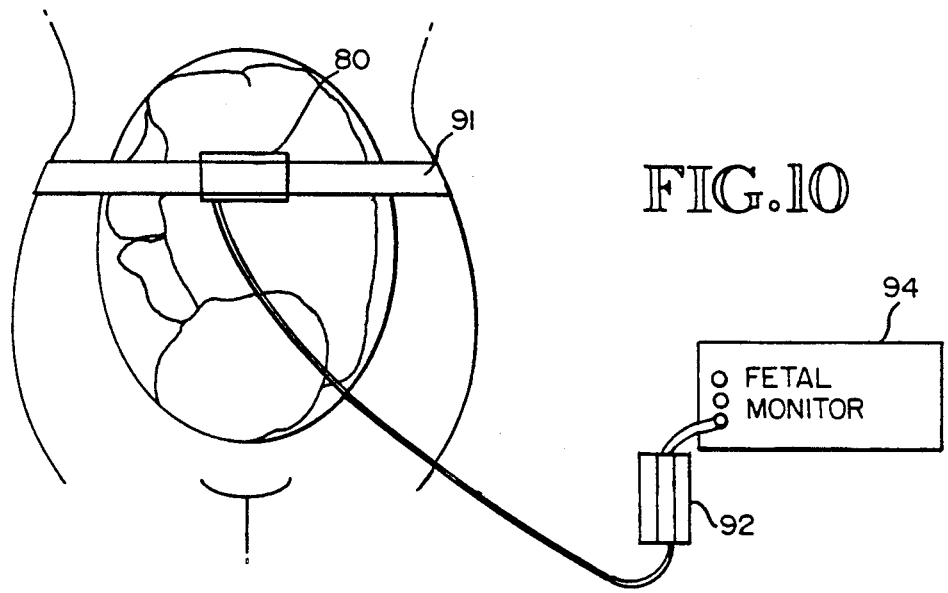
FIG.10

APPARATUS FOR NON-INVASIVE MONITORING OF UTERINE CONTRACTIONS

CROSS-REFERENCE TO RELATED APPLICATION

This is a continuation-in-part of application Ser. No. 142,943, filed on Jan. 12, 1988, now abandoned which in turn was a continuation-in-part of application Ser. No. 857,021, filed on Apr. 29, 1986 (abandoned).

Technical Field

This invention relates generally to the art of fetal monitoring apparatus and more particularly concerns apparatus for sensing uterine activity, in particular, contractions.

Background Art

Fetal monitors, which are typically quite sophisticated, are widely used to monitor the uterine activity of pregnant women, as well as the condition of the fetus in utero. Analysis of uterine contractions, in conjunction with fetal heart rate, during both pregnancy and labor, yields significant information concerning the condition of the fetus as well as the advancement of labor. Such monitoring is particulary helpful in so-called "difficult" pregnancies to systematically evaluate fetal stress, but is certainly also useful in more routine pregnancies.

Information indicating fetal distress will result in prompt remedial action, including caesarean delivery, both during pregnancy and/or during actual labor. Examples of currently available fetal monitors include the FetaScan from International Biomedics, Inc., the Corometrics 115 and the Hewlett-Packard 8040A.

Such fetal monitors, however, regardless of their sophistication, require a device or element to actually sense the uterine contractions. In a contraction, the abdomen hardens, and the shape of the abdomen changes, in part because the muscles in the anterior ligament of the uterus pull it forward during the contraction action.

One example of such a sensing element is a catheter which is capable of measuring uterine activity within the uterine cavity itself. U.S. Pat. No. 3,599,628 to Abbenante et al is an example of such a sensing element. Such devices, however, are invasive and position sensitive, i.e. they must be positioned adjacent the fetus for good results. Thus, movement of the fetus will frequently adversely affect the results.

Other devices, known as tocotonometers, are capable of non-invasively sensing uterine activity and are therefore widely used with fetal monitors. Tocotonometers measure the hardness of the abdominal wall, which is an indication of uterine activity, by various mechanical means. In use, the tocotonometer is held adjacent the patient,s abdomen, usually by a belt-like device, in the vicinity of the fundus, i.e. the top of the uterus. The tocotonometer is initialized by setting the recording level so that it is near zero between contractions. The output of the device is applied to the fetal monitor.

In use, however, tocotonometers have proven to be rather uncomfortable for the patient and require frequent adjustment as the fetus moves in the uterus. Other disadvantages include the fact that they are expensive, are rather delicate structurally and in operation, and are difficult to clean.

DISCLOSURE OF THE INVENTION

Accordingly, the present invention is an apparatus for detecting uterine activity which includes a pressurized bladder element; means for holding or maintaining the pressurized bladder against the abdomen of a patient in such a manner that the bladder creates an initial pressure against the patient,s abdomen, wherein the initial pressure is such that, when the abdomen of the patient hardens due to a uterine contraction, an increase in pressure in the bladder element results, which indicates uterine activity. The apparatus also includes a means for monitoring the pressure in the bladder element.

BRIEF DESCRIPTION OF THE DRAWINGS

FIG. 8 is a top view of a further embodiment of the present invention.

FIG. 9 is a longitudinal cross section of the article of FIG. 8.

FIG. 10 is a schematic view showing the article of FIG. 8 in place on the abdomen of a user, connected to a fetal monitor.

BEST MODE FOR CARRYING OUT THE INVENTION

Figure 1:
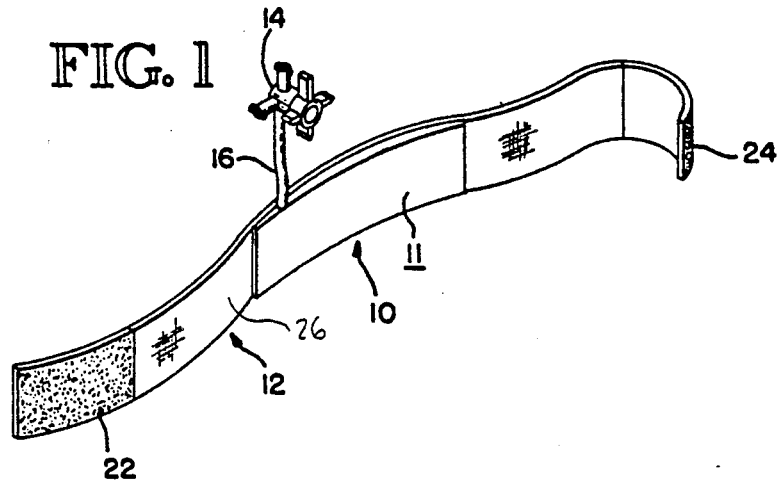
FIG. 1 is a schematic view of the apparatus of the present invention.
Figure 2:
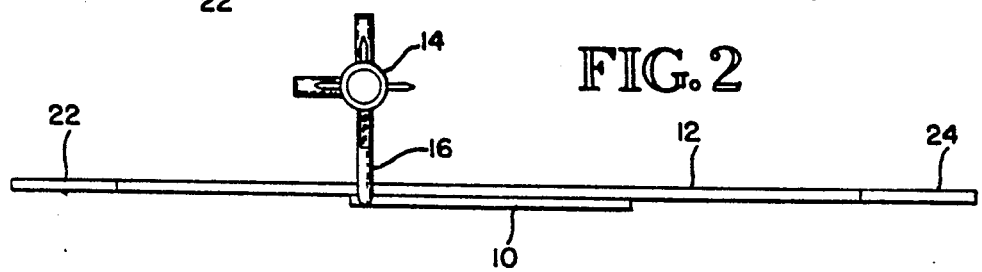
FIG. 2 is an elevation view of the apparatus of FIG. 1.

Referring to FIGS. 1 and 2, the invention generally includes a bladder element 10 which is secured to a patient's abdomen by a belt 12. The bladder 10 is pressurized by fluid through a conventional threeway stopcock or valve 14 or similar device which in turn is connected to the bladder 10 by a tube 16. A conventional pressure monitoring device 18 is also connected to stopcock 14 for monitoring of the pressure in the bladder 10.

Briefly, a uterine contraction will harden the abdomen and will pull the abdomen forward against the inner surface 11 of the bladder adjacent the abdomen, creating an increase in pressure on the fluid in the bladder, because the opposing outer surface of the bladder 10 abuts against the belt 12. The change in fluid pressure in the bladder 10 will be sensed by pressure monitor 18, which in turn applies the resulting pressure change information in the form of an electrical signal to the fetal monitor 19.

More specifically, the bladder element 10, in the embodiment shown, is generally rectangular in configuration, approximately 2 inches by 4 inches, and is comprised of a pliable material such as polyethylene or nylon-backed vinyl, with a wall thickness of 0.003 inches. When inflated by a fluid, the thickness of the bladder 10 will be approximately ¾ inch. Examples of appropriate fluids include both air and water. The bladder 10 can also be adapted to receive a sponge or similar element which is itself filled with fluid. In any event, the bladder 10 is designed so that a change in pressure on the bladder, and hence on the fluid therein, such as caused by a uterine contraction, can be readily detected.

The pressure monitor 18 is a commercially available element which includes strain gauge apparatus which is pressure sensitive and produces a corresponding electrical signal output. The fluid pressure in the bladder is communicated to the pressure monitor 18 by a length of tube 16. Preferably, the monitor 18 is located as close as reasonably possible to the bladder element 10.

Figure 5:
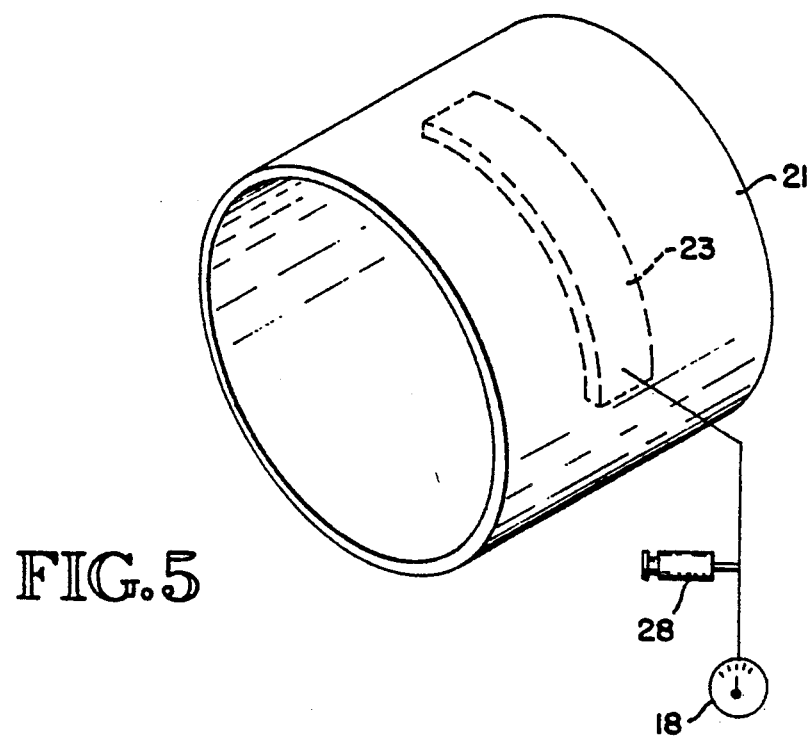
FIG. 5 is a schematic view showing another embodiment of the present invention.

The output of the pressure monitor 18 is an electrical signal which is applied to the fetal monitor 19. The pressure monitor 18 in FIG. 3 may include a pressure display, such as shown in FIG. 5. Usually such a display will not be necessary, however, as the output of the pressure monitor typically will be directed to a fetal monitor. However, in certain situations, it may be desirable to use the apparatus strictly as an indicator of uterine contractions, so that no actual fetal monitoring is necessary. In such a case, the pressure monitor 18 will have a display, so that it can provide direct indication of the occurrence of a contraction.

The belt 12 in the embodiment shown is approximately 36 inches long and 3 inches wide, and can be made from several different materials, including cotton and latex webbing. At the opposing ends of the belt 12 are attached velcro portions 22 and 24 which provide a capability for the belt to be conveniently and quickly secured around the abdomen of the patient. The bladder element 10 is secured by some means, such as mating velcro patches, to the interior surface 26 of the belt 12 so that when the belt is in place on the patient, the bladder is between the patient's abdomen and the belt. The belt 12 thus acts to firmly hold the bladder 10 against the patient's abdomen.

Figure 3:
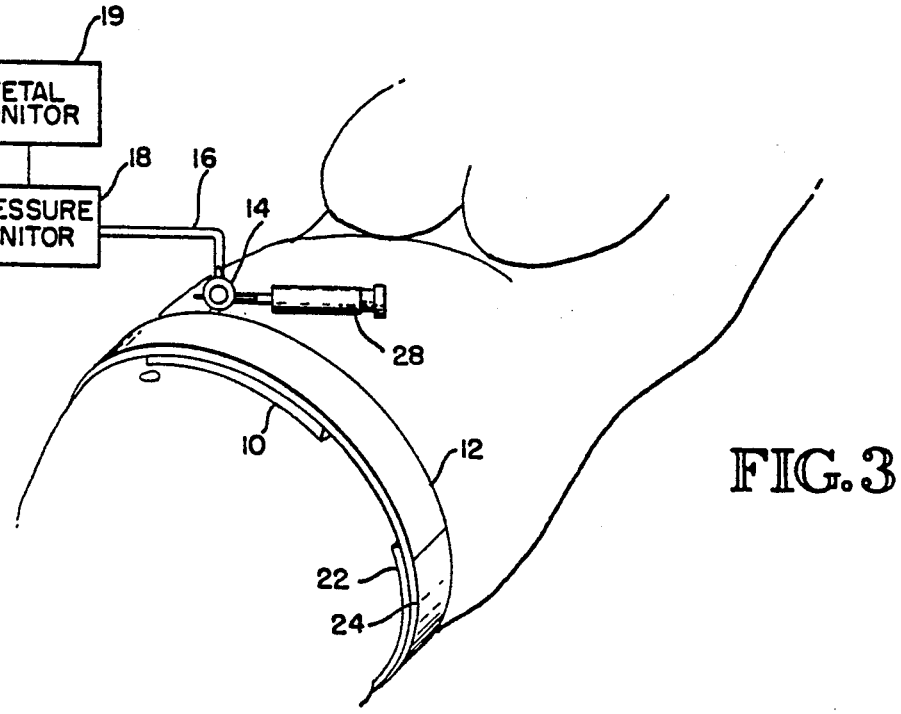
FIG. 3 is a schematic view showing the apparatus of FIG. 1 in position on a patient.

An alternative to the belt 12 shown in Figures 1-3 is a wide continuous loop of elastic material 21 which would fit around the abdomen of the patient, somewhat like a narrow body stocking, such as shown in FIG. 5. Such an element would be 8-10 inches wide and made from elastic latex webbing, with an interior layer of cotton. The element is tight enough to hold the bladder element 23 in place against the abdomen, without having the bladder element secured to the webbing. Since the webbing is continuous, no fastening is needed. This embodiment is advantageous in that it will not slide or otherwise move on the patient when the patient moves, as is sometimes the case with a belt.

The bladder 10 is in one embodiment first filled with fluid by means of a syringe 28 or the like to a pressure of approximately 10-20 torr, as determined by the pressure monitor 18, or a volume of 15-20 cc as indicated by the volume marks on the syringe. The belt and bladder combination is then positioned on the patient and secured. Alternatively, the bladder can be inflated with fluid after the unit has been secured to the patient.

Referring to FIG. 3, the bladder/belt combination is positioned so that bladder 10 rests on the patient's abdomen, in the vicinity of the top of the uterus. The ends of the belt 12 are moved around the patient and the velcro portions 22, 24 at the respective ends of the belt are joined to secure the belt to the patient. The bladder element 10 need not always be positioned close to the fetus for good results, and hence, the present invention is significantly less placement sensitive than other devices, such as tocotonometers, and hence are significantly more convenient for a technician to use.

Figure 4:
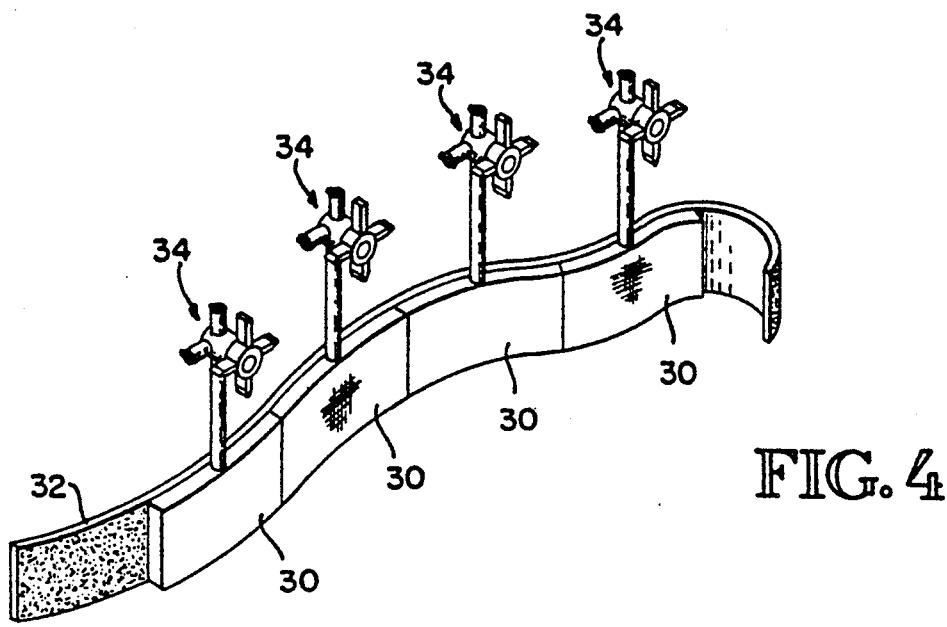
FIG. 4 is a schematic view of another embodiment of the present invention.

An alternative to the single bladder is the use of a plurality of bladder elements, with a single belt 32, as shown in FIG. 4. As an example, each bladder element 30 could be 1 inch by 3 inches, with the element being spaced along the belt. This alternative permits the direction of the contraction to be monitored, i.e. to follow the path of the contraction. Such an arrangement would also likely improve the sensitivity of the apparatus. The individual bladder elements 30—30 could be separately connected to their own individual pressurizing/monitoring apparatus through separate stopcocks 34—34, or several elements could be ganged together, or all of the elements could be connected to one pressurizing device and one monitor.

In operation of the apparatus of FIG. 1, a contraction will cause a change in pressure on the fluid in the bladder 10, and the pressure change will be detected by pressure monitor 18, the electrical output of which will change accordingly. The fetal monitor 19, to which the output information from the pressure monitor will be applied, will use that information to produce a visual record of the contractions, which in turn is typically used in conjunction with fetal heart beat information and certain other information to monitor fetal condition and progress of labor.

Figure 6:
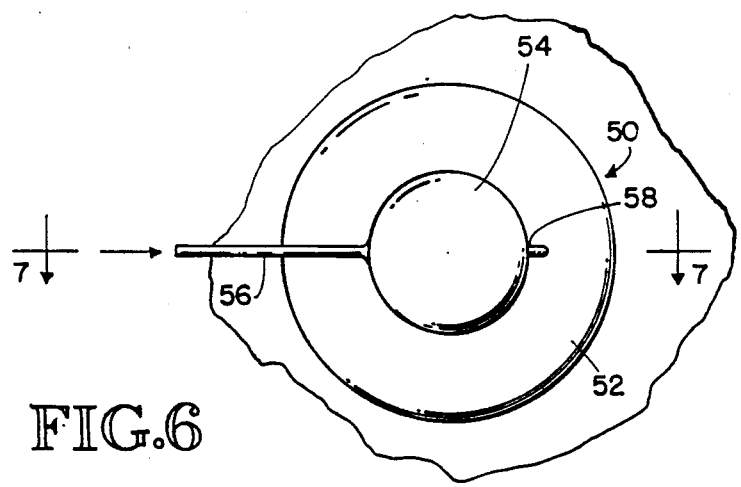
FIGS. 6 and 7 are top and cross-sectional views, respectively, of another embodiment of the present invention.
Figure 7:
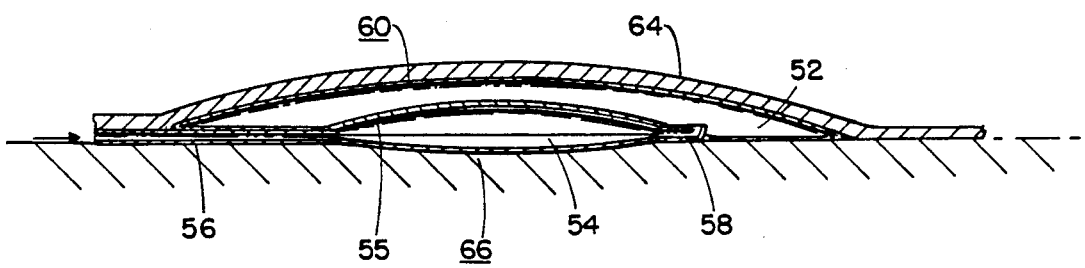

FIGS. 6 and 7 show another embodiment of the present invention. In this embodiment, the bladder element shown generally at 50 comprises a first circular bag or bladder 52, which in the embodiment shown has a diameter of approximately 4 inches, and a smaller, circular second bladder 54 which has a diameter of approximately 3 inches. Bladder element 50 is thus substantially smaller than the uterus which it is monitoring.

The second bladder 54 is positioned against a portion of one exterior surface 55 of the first bladder, approximately central thereof. Both the first and second bladders remain relatively flat when inflated and taper in thickness from a maximum at the center of the bladder to a minimum at the edge, although the first bladder 52 is somewhat compressed over the area covered by the second bladder, due to the pressure of the second bladder against the first bladder, as seen most clearly in FIG. 7. In the embodiment shown, the second bladder 54 varies in thickness from 1 inch at its center to a very small thickness at its edge. The thickness of the first bladder gradually increases from its center to a line coincident with the peripheral edge of the second bladder, where it is at a maximum, and then decreases from there to the edge of the first bladder.

An air tube 56 is connected to the outer edge of the second bladder, for inflation thereof, while an air tube or channel 58 connects the second bladder to the first bladder. In the embodiment shown, the tube 58 connects with the second bladder 54 at a point at the edge of the second bladder approximately 180° from the point at which tube 56 connects to the edge of the second bladder.

The back surface 60 of the first bladder opposite surface 55 abuts a belt 64 which may be secured around the abdomen of the patient. Typically, but not necessarily, the first bladder 52 is secured in some fashion to belt 64. The front surface 66 of second bladder 54 contacts the skin of the patient. The first and second bladders are made of a flexible material, such as latex rubber. The walls of the first and second bladders in the embodiment shown are 1/64 inch thick.

In operation, the second bladder 54 is filled with fluid, such as air, first. Fluid from bladder 54 then moves through channel 58 and fills bladder 52. In use, the nominal pressure in both the first and second bladders is approximately 15–20 torr. The second bladder 54, which is in contact with the skin of the patient, provides the indication of uterine activity, while the first bladder 52 performs the important function of maintaining the position of the second bladder on the abdomen of the patient. In particular, first bladder 52 tends to prevent lateral movement of the entire article, including the second bladder, on the skin surface of the patient, which is important in obtaining reliable, consistent results.

As described above, with respect to the embodiment of FIGS. 1 and 2, the belt 64 is tightened on the patient to the point where there is a relatively small pressure on the abdomen by the bladder element 50, sufficient to deform the abdomen slightly, as might be done by a clinician in a traditional physical monitoring of contractions.

The apparatus of the present invention is passive and has no effect on uterine function. When a uterine contraction actually occurs, the abdomen hardens, resulting in the abdomen "pressing back" against the initial pressure of the bladder element 50, in particular the smaller second bladder 54. The bladder element 50 thus provides a unidirectional sensing of uterine activity. The nominal pressure in the second bladder 54 can be referred to as a "set point" pressure, which in the embodiment shown is 15–20 Torr. The hardening of the uterus will cause a change in the pressure within the second bladder 54, away from the set point pressure, because the second bladder is positioned directly against the first bladder 52 which in turn abuts the bladder belt 64. The change in pressure in the second bladder is monitored, such as by a pressure monitor, as in the previous embodiments. A particular increase in pressure indicates the presence of a uterine contraction.

Although the preferred embodiment measures change in fluid pressure in the bladder element to ascertain a contraction, other changes in the bladder caused by a contraction could be used. For instance, a dimensional change of the bladder could be monitored automatically, as measured by an LED arrangement, or by measuring the change in capacitance through the bladder.

Another embodiment of the present invention is shown in FIGS. 8–10. In this embodiment, the tocotonometer shown generally at 80 includes an outer cover 82 and a sponge-like pad insert 84. In the embodiment shown, the pad insert 84 is 1 inch long by ⅜ inch wide by ¼ inch thick. The pad insert 84 is resilient, i.e. spring-like, and maintains an air volume within the cover 82. The pad 84 could be conventional sponge, or soft rubber or resilient foam. When pressure is applied to the article 80, referred to sometimes as a "bag" or "bladder", the pad insert deforms and the fluid pressure inside the bag increases. If the pad insert has a cellular structure such that in its non-deformed, i.e. rest, state, there is a significant amount of air within the insert itself, such air will be expelled from the pad upon deformation of the pad, also increasing the fluid pressure within the bag.

The cover 82 is 2 inches long by 1 inch wide in the embodiment shown, as seen most clearly in FIG. 8. The cover 82 therefore has dimensions such that there is a substantial amount of free air space between the sponge insert 84 and the cover 82. The cover 82 typically comprises a soft, non-plastic material, such as cotton, or soft wool or other similar material, for a comfortable contact with the skin of the patient. Such particular material is not necessary, however, to the function of the invention. The cover 82, is, however, substantially fluid-tight.

Attached to the back of the sponge insert 84, between the sponge insert 84 and the cover 82, is a rigid back plate 86 in the embodiment shown. However, it should be understood that satisfactory results can be obtained without the back plate. Back place 86 is secured to the back surface 87 of the sponge insert 84 and has outline dimensions similar to that of the sponge insert. The back plate 86 in the embodiment shown comprises a rigid plastic material and is approximately ⅛th inch thick. In use, the tocotonometer is positioned so that the back plate 86 is away from the skin of the patient, so that in effect the surface of the insert which is relatively away from the patient's skin is much stiffer than the surface which is adjacent the patient's skin. Typically, back plate 86 will be attached to the rear portion of the cover 82 by adhesive or other similar means.

Secured to the exterior surface 88 of the cover 82 in the vicinity of the back plate 86 is a stabilizing element 89, which acts as a connector for and accomplishes a stabilizing function for a belt 91 (FIG. 10) which secures the article 80 on the patient. In the embodiment shown, stabilizing element 89 is a Velcro strip. Alternatively, the article 80 could have loops through which a belt may be directed.

Extending from the tocotonometer is a fluid tube 90 which is connected to a monitoring interface, i.e. pressure sensor, 92 explained in more detail below, which in turn is connected to a conventional fetal monitor 94 or other display or recording device. Also, the output of the interface 92, comprising electrical signals which satisfy established standards for such devices, can be directed over telephone lines or the like so as to provide a remote monitoring capability for an at-home patient.

In use, the tocotonometer 80 is removed from its package (the tocotonometer is adapted for one time use and is intended to be disposable, for cleanliness reasons) and is attached to the belt 91 by means of the belt stabilizing element 89 on the rear surface 88 of the cover 82. The belt 90 and the tocotonometer 80 are positioned on the patient as shown in FIG. 10, with the tocotonometer being positioned against the abdomen of the patient in the manner explained above. The fluid tub 90 extends to a pressure sensor 92 which includes a strain gage for monitoring pressure changes within the tocotonometer, as with the other embodiments described above.

One of the advantages of the embodiment FIGS. 8–10 is that there is no necessity for an air syringe and stopcock shown with the other embodiments. There is sufficient air contained within the bag that when the tocotonometer and in particular the sponge insert 84 are compressed by contractions of the uterus, a change in the air pressure internal of the tocotonometer occurs, i.e. in the internal space between the cover 82 and the sponge insert 84.

The output of the pressure sensor 92 is applied to a conventional fetal monitor 94 (or other display) which produces a readout, such as in the form of a strip chart, of the pressure changes. The readout can then be interpreted as indicating the presence of a uterine contraction.

One of the advantages of the embodiment of FIGS. 8–10 is that the article is disposable. Further, the article is ready for use without requiring any initial fluid pressurization and is comfortable to the patient and nonbreakable as well as having a low profile. Still further, the article is easy to use and reliable and can be used with any existing fetal monitor or other display, due to the standardized signal output of the pressure sensor 92.

Thus, a sensing element for uterine contractions has been disclosed which is convenient to use, relatively inexpensive, and which is not particularly sensitive to correct placement on the abdomen to achieve good results.

Although a preferred embodiment of the invention has been disclosed herein for illustration, it should be understood that various changes, modifications and substitutions may be incorporated in such embodiment without departing from the spirit of the invention, as defined by the claims which follow.

I claim:

1. An apparatus for detecting uterine activity comprising:
   a bladder-like member which includes an substantially air-tight cover member which defines an interior volume and a resilient insert element, disposed within the interior volume;
   means for monitoring fluid pressure within the defined volume; and
   a fluid conduit connecting the interior volume with the pressure monitoring means, wherein, when the bladder-like member is positioned against the abdomen of a patient in the vicinity of the uterus by a belt or similar article in such a manner that an initial pressure is produced against the patient's abdomen by the bladder-like member and the patient's abdomen hardens due to a uterine contraction, a change in the fluid pressure in the interior volume results, thereby indicating the presence of uterine activity.

2. An apparatus of claim 1 wherein the outline of the insert element is such that there exists a space between the insert element and the cover member and the fluid conduit is in fluid communication with said space.

3. An apparatus of claim 1, including a rigid back plate attached to one surface of the insert element.

4. An apparatus of claim 3, wherein the outline of the back plate has substantially the same configuration and dimensions as the insert element.

5. An article for use in detecting uterine activity, comprising:
   a substantially air-tight cover member which defines an interior volume;
   a resilient insert element, disposed within the interior volume; and
   fluid conduit means for connecting the interior volume with a fluid pressure monitoring means, wherein, when the article is positioned against the abdomen of a patient and the abdomen hardens against the article due to a uterine contraction, a change in the fluid pressure in the interior volume results, indicating the presence of uterine activity.

* * * * *